United States Patent [19]

Kretschmann et al.

[11] Patent Number: 5,552,454
[45] Date of Patent: * Sep. 3, 1996

[54] NEW MATERIALS FOR BONE REPLACEMENT AND FOR JOINING BONES OR PROSTHESES

[75] Inventors: Josef Kretschmann, Langenfeld; Wolfgang Ritter, Haan; Johann-Friedrich Fues, Grevenbroich, all of Germany

[73] Assignee: Henkel Kommanditgesellschaft auf Aktien, Duesseldorf, Germany

[*] Notice: The portion of the term of this patent subsequent to Sep. 1, 2009, has been disclaimed.

[21] Appl. No.: 334,633

[22] Filed: Nov. 4, 1994

Related U.S. Application Data

[63] Continuation of Ser. No. 48,563, Apr. 16, 1993, abandoned, which is a continuation of PCT/EP89/00893, Jul. 31, 1989, abandoned.

[30] Foreign Application Priority Data

Aug. 9, 1988 [DE] Germany .......................... 38 26 915.5

[51] Int. Cl.$^6$ ................ A61F 2/02; A61F 2/28; A61K 31/74
[52] U.S. Cl. .................. 523/113; 424/78.18; 424/426; 623/16
[58] Field of Search ...................... 424/422, 423, 424/426, 78.37, 78.18; 623/16; 523/115

[56] References Cited

U.S. PATENT DOCUMENTS

| | | | |
|---|---|---|---|
| 2,362,511 | 11/1944 | Teeters | 260/78 |
| 3,773,919 | 11/1973 | Boswell et al. | 424/19 |
| 3,899,556 | 8/1975 | Heide et al. | 264/44 |
| 3,919,773 | 11/1975 | Freeman | 32/10 A |
| 4,010,196 | 3/1977 | Tsuk | 260/484 A |
| 4,011,312 | 3/1977 | Rueter et al. | 424/78 |
| 4,118,470 | 10/1978 | Casey et al. | 424/19 |
| 4,443,430 | 4/1984 | Mattei et al. | 424/78 |
| 4,563,489 | 1/1986 | Urist | 524/21 |
| 4,636,526 | 1/1987 | Dorman et al. | 623/16 |
| 4,645,503 | 2/1987 | Lin et al. | 623/16 |
| 4,842,604 | 6/1989 | Dorman et al. | 623/16 |
| 4,843,112 | 6/1989 | Gerhart et al. | 623/16 |
| 5,143,730 | 9/1992 | Fues et al. | 523/115 |

FOREIGN PATENT DOCUMENTS

| | | | |
|---|---|---|---|
| 250994 | 1/1988 | European Pat. Off. | |
| 2620891 | 11/1977 | Germany | 623/16 |
| 3229540 | 8/1982 | Germany | |
| 3825211 | 7/1988 | Germany | |
| 1163135 | 6/1989 | Japan | |
| 1593288 | 9/1977 | United Kingdom | |

*Primary Examiner*—Carlos Azpuru
*Attorney, Agent, or Firm*—Ernest G. Szoke; Wayne C. Jaeschke; Daniel S. Ortiz

[57] ABSTRACT

The invention relates to at least partly resorbable materials for replacing and/or joining bones and auxiliaries for implanting prosthesis material in living bone tissue which contain as their essential components body-compatible ceramic materials in admixture with body-resorbable oligomers and/or polymers of lower hydroxycarboxylic acids, more particularly glycolic acid and/or lactic acid (resin component) and which are characterized in that the resin component is produced using molecular-weight-regulating co-reactants from the class of mono- or polyfunctional carboxylic acids or corresponding alcohols and is substantially freed from free carboxyl groups.

27 Claims, No Drawings

NEW MATERIALS FOR BONE REPLACEMENT AND FOR JOINING BONES OR PROSTHESES

This application is a continuation of application Ser. No. 08/048,563 filed on Apr. 16, 1993, now abandoned, which is a continuation of PCT/EP89/00893 filed Jul. 31, 1989, now abandoned.

This invention relates to an improved composite material which may be used with advantage as a material for bone replacement or for joining bones and for implanting prosthesis material in living bone tissue. More particularly, the invention relates to the combination of known body-compatible ceramic materials, more particularly corresponding bioactive materials based on calcium phosphate, together with selected oligoesters which are also compatible with the body and which can be resorbed by the human and animal body.

These materials form a composite with the bone in the body and temporarily perform a supporting function. In the course of their resorption, they are replaced by the body's own osteogenic tissue which is subsequently converted into calcified, self-supporting bone tissue in the course of the natural bone regeneration process. Materials of this type may be widely used in orthopaedic surgery and orthodontic surgery to assist in the regeneration of parts of the skeleton damaged by accidents or disease, for example accident-damaged parts of tubular bones, after osteotomy and the like.

In the search for a suitable bone substitute material for unstressed or predominantly compression-stressed bone sections, for example in the surgical treatment of contour defects in the jaw/face region, ceramic materials based on calcium phosphate compounds have recently been acquiring significance, cf. for example Fischer-Brandies et an "Knochenersatzwerkstoff Hydroxylapatit (Bone Substitute Material Hydroxyl Apatite)", Colloquium med. dent. "Der Zahnarzt" 30 (1986), 567–583.

Considerable problems are involved in the practical use of such bone substitute materials which, in particular, are often available in pellet or granular form. It is not simply a question of finding a material which has sufficient stability; the bone substitute material must also be formable so that the bone can be restored at least substantially to its original shape. A biological requirement which has to be satisfied in this regard is that the implantate should take without any reaction and should not initiate any pathological tissue reactions, even after prolonged residence. The implantate should retain its shape and structure until it is replaced by the body's own bone. When used in the maxillary region, the material often has to allow prosthesis stressing as well.

Ceramic materials having different resorption rates based on calcium phosphates, more particularly tricalcium phosphate "TCP" and also pentacalcium hydroxide triphosphate ("hydroxyl apatite"), are now available for surgical use, particularly in sintered form. The sintered materials are distinguished by large apatite crystals and, in some cases, by additional fusion of the individual particles into a relatively large composite. The corresponding materials thus show increased resistance in biological medium. The ceramics differ in their porosity or density according to the particular production process used and the sintering temperature applied and contain both micropores (in the range from 1 μm up to about 100 μm in size) and larger macropores.

According to the literature reference cited at the beginning, a comparatively fine-particle to granular material of the type in question is used—for example in the maxillary region for restoring bone sections which have retained their continuity—by separating the gums from the bone and forming a cavity which is filled to the required extent with pelletized and/or granulated replacement material based on calcium phosphate. The opened periodontal pocket is then stitched and holds the filler in the required place.

Potential difficulties can exist in regard to the shaping required. The free-flowing, fine-particle ceramic material has no dimensional stability of its own, but instead adapts itself to the predetermined shape of the tissue pocket formed. Shifting of the pocket filling can occur at a later stage before the replacement material has been adequately stabilized by new bone tissue growing in. On the other hand, if the suture is involuntarily opened, partial loss of the filling introduced can occur.

Considerably earlier proposals (cf. DE-OS 26 20 890 and DE-OS 26 20 891) describe partly or completely resorbable bone replacement, bone joining or prosthesis anchoring compounds which combine sintered calcium phosphates either with soft plastic organic materials or with solid, hard polymer compounds. It is intended in this way to form on the one hand kneadable plastic materials and, on the other hand, hard materials which can be implanted in the living organism as solid materials. The particular continuous organic phase used in these composite materials may consist of bioresistant or resorbable or biodegradable polymers. Examples of this organic phase include polyesters of glycolic acid, lactic acid, polyamides of α-aminoacids, unmodified or modified natural polymers, such as gelatine or starch, triglycerides of higher alkane carboxylic acids or esters of polyhydroxy compounds and polymethyl methacrylate and polycyanoacrylate. The corresponding hard shaped structures are made in particular by impregnating the porous ceramic material with the polymer-forming monomer and then polymerizing the organic starting components in situ in the presence of the ceramic material.

The models portrayed in these earlier publications have never been adopted for use in dentistry. One possible explanation is that the organic component of these organic/inorganic composite materials is, after all, more important than was originally assumed in the reactions occurring in the living organism. The compatibility of such implantates and their intended function in the living organism is critically determined by the choice and quality of the resin-like organic phase used. It is only the appropriate specific development of precisely these organic polymer phases which ensures the desired synergistic cooperation between the three components of living organism, more particularly bone/phosphate ceramic/organic polymer phase.

Starting out from these difficulties, the invention seeks to provide improved composite materials of the described type which guarantee both easier handling and also rapid and safe "growing-in" of the fine-particle ceramic material introduced in direct contact with intact bone tissue. The problem addressed by the invention is solved by the use—together with the ceramic material—of selected oligomeric and/or polymeric polyester compounds which are compatible with the body and, in particular, can even be resorbed in the living organism and do not disturb the desired substitution process at the bone through unwanted secondary reactions, but instead—in one preferred embodiment—actually stimulate the substitution process and, in particular, are also capable of facilitating the shaping of the replacement material during the operation and of improving the dimensional accuracy of the implantate, particularly in the critical transition phase before adequate stabilization by the body's own bone tissue.

One of the objects of the invention in this regard is to enable composite materials of the described type to be reproducibly obtained in any quantities and in the same, predeterminable quality, the materials in turn being distinguished by optimal tissue compatibility and being obtainable by methods in which no auxiliary chemicals foreign to the body are used.

Accordingly, the present invention relates to at least partly resorbable materials for replacing and/or joining bones and to auxiliaries for implanting prosthesis material in living bone tissue, containing as essential components body-compatible ceramic materials in admixture with body-resorbable oligomers and/or polymers of lower hydroxycarboxylic acids, more particularly glycolic acid and/or lactic acid (hereinafter referred to as the "resin component"), the invention being characterized in that the resin component is produced using molecular-weight-regulating co-reactants from the class of mono- or polyfunctional carboxylic acids or corresponding alcohols and is substantially freed from free carboxyl groups.

A combination of elements for defining the resin component of the described composite materials is thus essential to the invention. This resin component is preferably synthesized from glycolic acid and/or lactic acid units linked in the manner of polyesters. However, the co-use of selected co-reactants makes it possible in known manner to establish the average molecular weight which is a determining factor for the period of survival of the resin component in the metabolism of the living organism. Finally, the invention presupposes the use of resin components of the described type which have been substantially freed from free carboxyl groups. This is an important element for the compatibility of the resin components used in accordance with the invention with the body and, in particular, with the tissue. Among the molecular-weight-regulating co-reactants, particular significance is attributed in one preferred embodiment of the invention to glycerol or selected glycerol partial esters, as will be described in more detail hereinafter.

So far as the type of body-compatible oligomers and/or polymers of hydroxycarboxylic acids is concerned, reference is made to DE-OS 32 29 540 (D 6652) and to applicants' associated, hitherto unpublished German patent applications P 37 16 302.7 (D 7890) and P 38 25 211.2 (D 8293). These patent applications relate to body-resorbable waxes which are intended in particular for the mechanical staunching of blood on the body's own hard tissue, preferably on bone, and which are distinguished by the fact that they consist of polyester oligomers or polymers of hydroxycarboxylic acids which are viscous to solid and wax-like at body temperature. Corresponding oligomers and/or polymers having an average molecular weight in the range from about 200 to 1500 and preferably in the range from about 300 to 1000 are particularly suitable for this application. The preferred polyester oligomers are formed from monohydroxycarboxylic acids which preferably contain 2 to 10 and, more preferably, 2 to 6 carbon atoms. Polyester oligomers of glycolic acid, lactic acid, hydroxypropionic acid, hydroxybutyric acid and/or hydroxybenzoic acid are mentioned in particular. The most important hydroxycarboxylic acids in practice for the synthesis of the viscous to solid polymer components in question are glycolic acid and/or lactic acid.

It has been found that these waxes and corresponding compounds of even higher molecular weight, which hitherto have mainly been proposed for the mechanical staunching of blood on bone, may advantageously be used in combination with mineral bone substitutes, more particularly of the type mentioned at the beginning. If, in particular, solid oligomers and/or polymers of the type mentioned are mixed with the fine-particle inorganic bone substitute in such quantities that the organic phase is present as the closed phase in the composite material, the invention provides a formable and, if desired, dimensionally stable material which may be combined as an implantate in any desired spatial form with the body's own bone tissue. The organic polyester phase is not only physiologically safe, it is also resorbed in the manner described in applicants' earlier patent applications cited above without any toxic degradation products being formed. At the same time and, in one preferred embodiment, largely synchronously therewith, the body's own bone substance is built up and the degradation-resistant inorganic particles are incorporated in the new tissue formed. It has been found in this regard that the co-use of the selected hydroxycarboxylic acid polyester materials according to the invention can even specifically stimulate the regeneration of bone tissue having the desired structure. It is clear that operations using bone substitutes based on calcium phosphate can be improved in many respects by the use of the composite material according to the invention.

More specifically, the disclosures of applicants' earlier applications cited above apply equally to the organic polyester phase of the composite materials according to the invention, but with the proviso that the average molecular weight is in a broader range in their case, typically in the range from about 200 to 10,000 and preferably in the range from about 300 to 5,000 g/mol.

The polyester oligomers having an average molecular weight in the above-mentioned range, which are preferably viscous to solid at body temperature, contain terminal co-reactants for regulating molecular weight. Particularly important hydroxycarboxylic acids for forming the polyester oligomer segments are the already mentioned glycolic acid, the isomeric lactic acids, the optionally isomeric α- or β-hydroxypropionic acids, the optionally isomeric α-, β- or γ-hydroxybutyric acids, o-hydroxybenzoic acid (salicylic acid), m-hydroxybenzoic acid and/or p-hydroxybenzoic acid (anisic acid). Certain isomers of the acids mentioned and also mixtures thereof may be used. The degradation rate of the wax by the body's own degradation reactions can be influenced to a considerable extent by using mixtures of different hydroxycarboxylic acids and, more particularly, by the use of glycolic acid and lactic acid together.

High polymers of the type described above and their use in the medical field are known. They typically have fiber properties. Their compatibility and degradability have been studied in detail. For example, synthetic fibrous materials based on polyglycolic acid and polylactic acid which can be resorbed in the organism are known, cf. for example U.S. Pat. Nos. 3,297,033; 3,422,871; 3,626,948; 2,668,162; 2,676,945 and 2,703,316. Further literature references on the use of high polymers such as these can be found in the above-cited DE-OS 32 29 540.

Monofunctional and/or polyfunctional alcohols or corresponding carboxylic acids are used as co-reactants in the preparation of the reaction product in order reproducibly to establish the particular degree of oligomerization and, hence, the required viscous to solid consistency of the reaction product. Suitable co-reactants and, in particular, examples of the important class of alcoholic co-reactants are again described in detail in the earlier applications cited above. Particular significance may be attributed in this regard to glycerol which may be used to optimize the tissue compatibility of the viscous to solid organic phase, as described in earlier application P 37 16 302.7 (D 7890). In addition to glycerol, significance is attributed to partial esters of glycerol with, in particular, alcohols containing 12 to 18 carbon atoms.

Where resorbable resins or waxes of the type in question are used, unwanted tissue damage can be avoided particularly safely when, through the production of the degradable wax, it is ensured that its content of non-reacted carboxyl groups is at least greatly reduced or, better still, almost completely eliminated. The statistical molecular weight distribution emanating directly from the production of the waxes always leaves a certain percentage of free carboxyl groups behind in the oligomeric reaction mixture, even when, basically, the desired average number value has been established for the molecular weight. In this case, too, free the carboxyl groups in question may emanate from free monomeric hydroxycarboxylic acids.

Various possibilities are available for reducing the content of free carboxyl groups in the organic phase. In one preferred embodiment of the earlier application P 37 16 302.7 (D 7890), the wax-like material is freed from its content of unreacted starting components to such an extent that the content of unreacted hydroxycarboxylic acids is reduced to residual contents below 0.5% by weight and preferably to residual contents below about 0.2% by weight. In general, the waxes used may contain residual contents of unreacted hydroxycarboxylic acids of or below 0.1% by weight. The removal of unreacted components or reaction products of undesirably low molecular weight from the oligomers initially formed may readily be achieved as follows: the educt initially formed is mixed with a water-miscible organic solvent, for example with acetone, methanol or ethanol or the like, and the suspension formed is subsequently introduced into a solvent which does not dissolve the desired oligomer fractions, but is an adequate solvent for unreacted components or reaction products of low molecular weight. Isopropanol has proved to be a particularly suitable precipitation medium for this second stage of the process. Thus, in one effective purification process, the oligomerization product initially formed and a solvent, such as acetone, methanol or the like, are mixed in a ratio of approximately 1:1 and intensively digested. The solid suspension formed is then introduced into several times, for example 7 to 12 times, its volume of isopropanol and filtered off. The liquid phase is filtered under suction, washed, best with isopropanol, and dried. The particulars of this purification process are of course meant to be purely exemplary and may be varied within the limits of specialist knowledge.

In another embodiment of the invention, the oligomerization product initially formed is freed from free carboxyl groups in a totally different way. In this embodiment, the free carboxyl groups are neutralized with suitable salt-forming, body-compatible cations, including above all alkali metals and/or alkaline earth metals, more particularly calcium and magnesium and, if desired, even aluminium. Relevant particulars can be found in applicants' above-cited earlier application P 38 25 211.2 (D 8293).

So far as the nature of suitable ceramic materials based on calcium phosphate and their chemical definition are concerned, reference is made to the publication by Fischer-Brandies et al which was cited at the beginning. The preferred ceramic material is sufficiently purified hydroxyl apatite and/or tricalcium phosphate. Other ions may be taken up into the crystal lattice in exchange, as mentioned in the cited literature reference. Sintered and, if desired, microporous and/or macroporous material or mixtures of such materials may be used.

In one preferred embodiment, the new composite material contains powder-form and/or granulated ceramic materials based on calcium phosphate in intimate admixture with the organic phase, the inorganic, fine-particle material being present as disperse filler phase in hydroxycarboxylic acid oligomer or polymer which surrounds the disperse filler as continuous or closed phase. In another embodiment, however, it is also possible to use composite materials of the inorganic and organic constituents mentioned in which the organic phase is used in such a limited quantity that the composite material basically retains a granular or fine-particle character, although cores of inorganic material of the described type are surrounded and—in the case of porous inorganic materials—may even be at least partly permeated by the organic component.

The first embodiment just described with the resin component as the continuous phase containing disperse ceramic particles may be in the form of a kneadable mass of which the kneadability is established if desired by the application of moderately elevated temperatures, although a dimensionally stable, solid mass is present at room temperature and preferably also at body temperature. However, this embodiment also encompasses materials which may be shaped by machining, i.e. by cutting, milling and the like. The second of the embodiments just described is a disperse bone substitute material in which the resin component is present at least as a coating of the individual particles, but if desired may even be absorbed into the interior of the individual particles. In this case, the development of predetermined three-dimensional forms is not of crucial importance to the use of the resin component, instead the sealing and/or filling of the porous structure of the inorganic material is the critical factor. On the one hand, it prevents unwanted residues of secretion and/or blood being trapped in the region of the wound, on the other hand the function of the resin component in stimulating bone regeneration is also in evidence in this form.

If the new composite materials are present as cohesive, optionally heat-formable compounds, powder-form calcium phosphate may be the sole ceramic material, in which case a range of about 100 to 200 μm may be regarded as the upper limit to the particle size of the powder-form materials. Bone-like, solid substitute materials of this type are formed in particular when the content of ceramic powder in these materials is at least about 30% by weight, preferably of the order of 40 to 80% by weight and, more preferably, in the range from about 40 to 65% by weight.

If, on the other hand, the composite materials according to the invention contain the ceramic materials in granular form, the following figures apply to the preferred particle sizes of the granules and to the particular mixing ratios used: the preferred particle diameter of the granules is in the range from about 0.1 to 3 mm, preferably in the range from about 0.1 to 2 mm and more preferably in the range from about 0.2 to 1 mm. The preferred granule content is in the range from about 20 to 70% by weight and preferably in the range from about 20 to 60% by weight, although particular significance can be attributed to the range from about 25 to 50% by weight. All the percentages by weight mentioned are based on the total weight of the composite material according to the invention.

In one particular embodiment of the invention, the ceramic materials are present in an at least partly bimodal particle size distribution, mixtures of powder and granules being particularly suitable. However, other combinations are also possible, including for example the use of a mixture of granules of different size. Through these measures, it is possible to establish predetermined combinations of properties or effects during the processing and/or residence of the composite material in the body. For example, it is possible in this way to regulate an "open pore diameter" for the piece of material as a whole, i.e. to regulate the average passage diameters which, when filled with the resin component, separate the ceramic materials from one another or join them to one another. It is thus possible to optimize the free space for the initial fresh bone growth which then leads in subsequent phases of the healing process to resorption and incorporation of even the ceramic component in the living organism.

Where at least bimodal particle size distributions of these ceramic materials are present, it may be preferred to use mixtures of powder and granules containing from about 5 to 30% by weight powder and from about 15 to 50% by weight granules (percentages by weight again based on the material as a whole).

One particularly preferred embodiment of the invention is characterized by the use of resin components based on the lower hydroxycarboxylic acids, more particularly glycolic and/or lactic acid, which have been prepared by condensation of monomeric starting elements in the absence of catalysts. It is known that this autocondensation of glycolic acid and lactic acid takes place under the effect of the carboxylic acid groups of the starting material which catalyze the esterification reaction. In this case, too, the reaction is carried out in the presence of the co-reactants regulating the desired molecular weight, more particularly in the presence of glycerol. The elimination of free carboxyl groups from the condensate in a final step, more particularly by salt formation with, for example, calcium and/or magnesium, is particularly important in these embodiments. If resin components such as these are mixed with the ceramic materials, the introduction of unwanted foreign elements into the composite material and, ultimately, into the living organism is optimally prevented. In this case, the polycondensation of the resin component may be carried out in known manner initially under normal pressure with removal of the water of reaction formed and, if desired, under an increasing vacuum in later stages of the polycondensation reaction.

The resin components may be mixed with the powder-form and/or granular ceramic materials in known manner. It is preferred in this regard to use the resin components in molten form. It can be of advantage, particularly where limited quantities of the resin component are incorporated in comparatively large quantities of the ceramic materials, to use inert auxiliary solvents for mixing the components, the solvents being removed on completion of mixing. Preferred solvents are solvents of sufficiently high volatility, such as acetone, readily volatile alcohols, esters and the like.

EXAMPLES

1. Preparation and description of the resorbable resin components a) Resins produced from glycolic acid/glycerol General procedure for the preparation of the reaction products of glycolic acid with glycerol:

Glycolic acid and glycerol are introduced into a three-necked flask equipped with a stirrer and distillation bridge. After blanketing with nitrogen, the contents of the flask are heated to 150° C. and the reaction is continued for 3 to 5 hours until no more water of reaction is eliminated. The flask is then carefully evacuated to 10 torr at a temperature of 150° C. After another 2 hours under these conditions, the reaction mixture is cooled to 100° C., the vacuum is eliminated and the product is neutralized as described in 2. below and packed in containers while still hot.

The composition of the reaction mixtures and the properties of the oligomers are shown in Table 1.

TABLE 1

| | Oligohydroxycarboxylic acids of glycolic acid and glycerol | | | | |
|---|---|---|---|---|---|
| | Educts | | Yield | Viscosity at | |
| Example | Glycolic acid mol | Glycerol mol | water of reaction % | the measuring temperature | Consistency |
| 1 | 8 | 1 | 100 | 2450 mPas/65–70° C. | Highly viscous, light yellow |
| 2 | 9 | 1 | 99.1 | 3950 mPas/65–70° C. | Soft, paste-like, yellowish |
| 3 | 12 | 1 | 99.0 | — | Hard, white | b) Resins produced from lactide and glycerol

General procedure for the preparation of the reaction products of lactide and glycerol Lactide (L(–)-Lactid N, a product of Böhringer Ingelheim) and glycerol were introduced into a standard laboratory reactor and heated with stirring under nitrogen over a period of 1 hour to a temperature of 195° C. The mixture was then left to react for three hours at 195° C. and, after neutralization as described in 2., was packed in containers while still hot. An Sn(II) chloride solution in ether was added as catalyst (7 ml of a solution of 2.5 g $SnCl_2$ in 1000 ml ether for the reaction of 3 mol lactide with 1 mol glycerol).

The composition of the reaction mixtures and the properties of the oligomers are shown in Table 2.

TABLE 2

Oligohydroxycarboxylic acids of glycerol and lactide

| Example | Educts Glycerol mol | Lactide mol | Consistency | Viscosity at 65–70° C. | Free lactic acid content (% by weight) |
|---|---|---|---|---|---|
| 4 | 1 | 5 | Soft, clear | 2500 mPas | 0.125% |
| 5 | 1 | 8 | Solid, brittle, clear | 6000 mPas | — |

2. Procedure for filling the resins and properties of the mixtures

The free acid (glycolic acid/lactic acid) content of the resins described in 1. was determined by titration. The free acid was neutralized by addition of an equimolar quantity of $CaCO_3$ and intensive mixing.

Hydroxyl apatite was added to a melt of the neutralized resins with stirring at temperatures of 120° C. (low filling) to 160° C. (high filling), followed by intensive mixing for 15 minutes. The resins proved difficult to fill with more than 60% hydroxyl apatite. To this end, the resin was dissolved in acetone (1:1), filled with hydroxyl apatite while stirring and the solvent was subsequently evaporated.

After cooling (storage for 24 hours in an aluminium dish), consistency was evaluated and Shore hardness was measured.

The results are shown in Tables 3 to 7 below.

TABLE 3

Properties of the filled systems

| Resorbable resin No. 1 (glycolic acid/ glycerol 8:1) | Degree of filling % by weight | Filler and properties Consistency | Shore A hardness |
|---|---|---|---|
| | | Sintered hydroxyl apatite ganules, particle size 0.25–0.5 mm | |
| a | 10 | Non-cohesive two-phase mixture of wax and sedimented apatite | — |
| b | 20 | | — |
| c | 30 | | — |
| d | 40 | Homogeneously filled flexible mass | 46 |
| e | 50 | | 47 |
| f | 60 | | 64 |
| g | 70 | Granules wetted with resin | — |
| | | Sintered hydroxyl apatite granules, particle size 0.50–1.0 mm | |
| h | 50 | Homogeneously filled flexible mass | 75 |
| i | 60 | | 68 |
| j | 70 | | 81 |
| k | 80 | Granules wetted with resin | — |

TABLE 4

Properties of the filled systems

| Resorbable resin No. 2 (glycolic acid/ glycerol 9:1) | Degree of filling % by weight | Filler and properties Consistency | Shore A hardness |
|---|---|---|---|
| | | Hydroxyl apatite powder | |
| a | 10 | Wax-like, formable | 37 |
| b | 20 | Wax-like, formable | 46 |

TABLE 4-continued

Properties of the filled systems

| Resorbable resin No. 2 (glycolic acid/ glycerol 9:1) | Degree of filling % by weight | Filler and properties Consistency | Shore A hardness |
|---|---|---|---|
| c | 30 | Wax-like | 76 |
| d | 40 | Wax-like | 78 |
| e | 70 | Non-cohesive, very brittle solid | 5 |
|   |    | Sintered hydroxyl apatite granules, particle 0.25–0.5 mm | |
| f | 40 | Two-phase mixture (sedimented apatite) | — |
| g | 50 | Homogeneously filled, hard mass | 53 |
| h | 55 | Homogeneously filled, hard mass | 67 |
| i | 60 | Homogeneously filled, hard mass | 57 |
|   |    | Sintered hydroxyl apatite granules, particle size 0.50–1.0 mm | |
| j | 50 | Homogeneously filled hard mass | 64 |

TABLE 5

Properties of the filled systems

| Resorbable resin No. 3 (glycolic acid/ glycerol 12:1) | Degree of filling % by weight | Filler and properties Consistency | Shore A hardness |
|---|---|---|---|
|   |    | Sintered hydroxyl apatite granules, particle size 0.25–0.5 mm | |
| a | 40 | Two-phase mixture of resin and sedimented apatite | — |
| b | 50 | Homogeneously filled hard mass | 57 |
| c | 60 | Homogeneously filled hard mass | 54 |
|   |    | Sintered hydroxyl apatite granules, particle size 0.50–1.0 mm | |
| d | 50 | Homogeneously filled hard mass | 71 |

TABLE 6

Properties of the filled systems

| Resorbable resin No. 4 (lactide/ glycerol 5:1) | Degree of filling % by weight | Filler and properties Hydroxyl apatite powder Consistency | Shore A hardness |
|---|---|---|---|
| a | 10 | Wax-like, formable | 27 |
| b | 20 | Wax-like, formable | 38 |
| c | 30 | Wax-like, formable | 65 |
| d | 40 | Wax-like | 72 |
| e | 50 | Wax-like | 78 |
| f | 70 | Non-cohesive, very brittle solid | 12 |

TABLE 7

Properties of the filled systems

| Resorbable resin No. 5 (lactide/ glycerol 8:1) | Degree of filling % by weight | Filler and properties Consistency | Shore A hardness |
|---|---|---|---|
| | | Sintered hydroxyl apatite granules, particle size 0.25–0.5 mm | |
| a | 40 | ⎫ | 70 |
| b | 50 | ⎬ Homogeneously filled hard mass | 70 |
| c | 60 | ⎭ | 74 |
| | | Sintered hydroxyl apatite granules, particle size 0.50–1.0 mm | |
| d | 50 | Homogeneously filled hard mass | 74 |

Measuring methods/additives used

1) Shore A hardness was determined in accordance with DIN 53505, ASTM D 2240 (spike penetration depth) using the Zwick apparatus.

2) Hydroxyl apatite powder pentacalcium hydroxytriphosphate, $Ca_5(PO_4)_3(OH)$ Merck/Darmstadt Hydroxyl apatite sintered granules $Ca_5(Po_4)_3(OH)$ Heyl; Chem.-pharm. Fabrik/Berlin 37

3) Viscosity was determined with the following instrument: Epprecht type TVB torsional viscosimeter, measuring element 4, at 200 r.p.m./70° C. (heated samples).

We claim:

1. A composition for replacing bone, joining bones and for implanting prosthesis material in living bone tissue comprising: a particulate body-compatible ceramic material in admixture with at least one body-resorbable polymer of lower hydroxy-carboxylic acid monomers wherein a molecular weight of the polymer of from 200 to 10,000 grams per mol. is regulated by coreaction with at least one co-reactant selected from the group consisting of monocarboxylic acids, polycarboxylic acids, monohydroxyl alcohols and polyhydroxyl alcohols wherein the polymer contains not more than 0.5% by weight free carboxyl groups.

2. The composition of claim 1, wherein the coreactant is at least one member selected from the group consisting of glycerol and glycerol partial ester having at least one free hydroxyl group.

3. The composition of claim 2 wherein free carboxyl groups originally present in the body-resorbable polymer have been converted into body-compatible salt groups by reaction with at least one neutralizing compound of a metal selected from the group consisting of alkali metals, alkaline earth metals and aluminum.

4. The composition of claim 1 wherein the body compatible ceramic material comprises at least one bioactive ceramic material selected from the group consisting of resorbable, particulate calcium phosphate ceramics and non-resorbable calcium phosphate ceramics.

5. A resorbable composition of claim 1 wherein the ceramic material comprises granulated ceramic materials coated with the body resorbable polymer of lower hydroxy-carboxylic acid monomers wherein the molecular weight of the polymer is from 200 to 10,000 grams per mol and is regulated by coreaction with at least one co-reactant selected from the group consisting of monocarboxylic acids, polycarboxylic acids, monohydroxyl alcohols and polyhydroxyl alcohols.

6. The composition of claim 1 wherein the body compatible ceramic material comprises at least one member selected from the group consisting of unsintered tricalcium phosphate, unsintered hydroxyl apatite, sintered tricalcium phosphate and sintered hydroxyl apatite.

7. The composition of claim 1 which is a cohesive composite, Kneadable to solid at room temperature, wherein the body-resorbable polymer is a continuous phase. hydroxyl apatite, sintered tricalcium phosphate and sintered hydroxyl apatite.

8. The composition of claim 1 in the form of a disperse composite material wherein, the ceramic particles or agglomerates are coated with the body-resorbable polymer.

9. The composition of claim 1 which is a cohesive heat formable composition containing more than about 30% by weight of the ceramic material solely in powder form.

10. The composition of claim 1 which is coherent, containing from about 20% to about 60% by weight of the composition of ceramic material with the form of granules.

11. The composition of claim 1 wherein, the ceramic material is present in a bimodal particle size distribution comprising a mixture of powder and granules in which the powder makes up about 5 to 30% by weight and the granules make up about 15 to 50% by weight, based on the weight of the composition.

12. The resorbable composition of claim 1 wherein the polymer is formed from at least one monomer selected from the group consisting of glycolic acid and lactic acid said polymer being produced by polycondensation of the monomeric hydroxycarboxylic acids in the absence of foreign catalysts.

13. The composition of claim 1 wherein the body-resorbable polymer comprises residues of at least one monomer selected from the group consisting of lactic acid and glycolic acid.

14. The composition of claim 2 wherein the glycerol partial esters comprise partial esters of glycerol with monocarboxylic acids having from 12 to 18 carbon atoms.

15. The composition of claim 3 wherein the neutralizing metal compound is a calcium compound.

16. The composition of claim 4 wherein the ceramic material comprises calcium phosphate powder.

17. The composition of claim 4 wherein the ceramic material comprises granules of calcium phosphate.

18. The composition of claim 5 wherein the porous granules contain the body-resorbable polymer.

19. The composition of claim 7 which is kneadable to solid at body temperature, containing the ceramic material present as a homogenous dispersion.

20. The composition of claim 8 wherein the ceramic particles contain the body-resorbable polymer.

21. The composition of claim 1 wherein the body-resorbable polymer has an average molecular weight in the range of from about 300 to about 5,000 grams/mol.

22. The composition of claim 9 wherein the ceramic material is a powder with a particle size below about 100 μm.

23. The composition of claim 22 containing from about 40 to about 65% by weight of the powder ceramic material.

24. The composition of claim 10 containing from about 20% to about 60% by weight of the composition, of the ceramic granules.

25. The composition of claim 24 containing from about 25% to about 50% by weight of granules having a particle size of from about 0.2 to about 1.0 mm.

26. The composition of claim 1 containing not more than 0.2% by weight free carboxyl groups.

27. The composition of claim 1 containing not more than 0.1% by weight free carboxyl groups.

* * * * *